(12) United States Patent
Goenka et al.

(10) Patent No.: US 10,905,598 B2
(45) Date of Patent: Feb. 2, 2021

(54) TAMPON WITH CONSOLIDATED FIBROUS ASSEMBLY AND METHOD OF MAKING

(71) Applicant: WELSPUN INDIA LIMITED

(72) Inventors: Dipali Goenka, Mumbai (IN); Pranay Sahu, Mumbai (IN)

(73) Assignee: Weslpun India Limited, Maharashtra (IN)

(*) Notice: Subject to any disclaimer, the term of this patent is extended or adjusted under 35 U.S.C. 154(b) by 432 days.

(21) Appl. No.: 15/280,709

(22) Filed: Sep. 29, 2016

(65) Prior Publication Data
US 2017/0354545 A1 Dec. 14, 2017

(30) Foreign Application Priority Data
Jun. 10, 2016 (IN) .............................. 201621019956

(51) Int. Cl.
| | | |
|---|---|---|
| *A61F 13/15* | (2006.01) | |
| *A61F 13/20* | (2006.01) | |
| *A61F 13/34* | (2006.01) | |
| *A61F 13/53* | (2006.01) | |
| *A61L 15/22* | (2006.01) | |
| *D01D 5/098* | (2006.01) | |
| *D04H 5/03* | (2012.01) | |

(52) U.S. Cl.
CPC ........ *A61F 13/2082* (2013.01); *A61F 13/206* (2013.01); *A61F 13/2054* (2013.01); *A61F 13/2068* (2013.01); *A61F 13/2071* (2013.01); *A61F 13/2085* (2013.01); *A61F 13/34* (2013.01); *A61F 13/53* (2013.01); *A61L 15/225* (2013.01); *D01D 5/0985* (2013.01); *D04H 5/03* (2013.01); *A61F 2013/53035* (2013.01); *A61F 2013/530226* (2013.01); *A61F 2013/530379* (2013.01); *D10B 2201/02* (2013.01); *D10B 2509/00* (2013.01)

(58) Field of Classification Search
CPC .............. A61F 13/2082; A61F 13/2054; A61F 13/206; A61F 13/2068; A61F 13/2071; A61F 13/2085; A61F 13/34; A61F 13/53; A61F 2013/530226; A61F 2013/53035; A61F 2013/530379
See application file for complete search history.

(56) References Cited

U.S. PATENT DOCUMENTS

| | | | | |
|---|---|---|---|---|
| 2003/0120225 | A1* | 6/2003 | Everhart ........... | A61F 13/47209 604/285 |
| 2007/0260211 | A1* | 11/2007 | Schmidt-Forst ...... | A61F 13/206 604/385.17 |
| 2008/0262463 | A1* | 10/2008 | Noel ................... | A61F 13/2051 604/385.18 |

* cited by examiner

*Primary Examiner* — Jacqueline F Stephens
(74) *Attorney, Agent, or Firm* — Offit Kurman, PA; Gregory A. Grissett

(57) ABSTRACT

The present disclosure describes a tampon article, a composite fibrous web, and a method of making same. Such an article includes an outer carrier component including an inner surface that defines an internal void. Including an absorbent component elongate along an axis and is disposed in the internal void. The absorbent component includes an outer surface that extends about the axis and faces the inner surface. The absorbent component further includes a composite fibrous web of staple cellulosic fibers and a meltspun web of filaments entangled with the web of staple cellulosic fibers. The composite fibrous web can be in a compressed configuration in the internal void such that at least portion of the outer surface of the absorbent component is defined by the meltspun web of filaments. The tampon can include a withdrawal cord coupled to the absorbent component.

26 Claims, 4 Drawing Sheets

TAMPON WITH CONSOLIDATED FIBROUS ASSEMBLY AND METHOD OF MAKING

TECHNICAL FIELD

The present disclosure relates to an absorbent article, such as a tampon, and a consolidated fibrous assembly for use in same.

BACKGROUND

Tampons are used to absorb bodily fluids. A typical tampon includes an absorbent core material and a permeable covering or overwrap that surrounds the absorbent core. The absorbent core and a permeable covering are together compressed into a cylindrical structure, sometimes referred to as a pledget, placed within an outer tube. An applicator may be placed in the outer tube adjacent to the absorbent core. Other versions do not use applicators. In use, the tampon is inserted into the vagina and the compressed pledget is ejected out an insertion end of the outer tube. The covering can aid insertion into the vaginal cavity. The outer tube and applicator, if present, are withdrawn leaving the pledget and withdrawal cord in place. The absorbent core expands upon exposure to bodily fluids and also absorbs the fluids.

Tampon manufacturing processes are complex and balance cost considerations with performance requirements. Significant cost pressure is placed upon tampon manufacturers and raw material suppliers. Efforts to realize costs savings have focused on productivity gains through greater process efficiencies along the supply chain. Other efforts focus on reducing the amount of raw material used per tampon, which should result in per unit cost savings. These cost saving measures are balanced against the performance requirements of the tampon that include sterility, safety, high absorbency, and ease of use.

Other considerations in balancing cost and performance are related to process control. Inadequate process controls can decrease efficiency and may manifest problems during use. For example, if the covering is not adequately secured around the absorbent core, subsequent handling may cause separation of the covering from the absorbent core. This creates a risk of exposing the absorbent materials in the core directly to the vaginal cavity in use. Work continues to improve tampon manufacturing processes.

SUMMARY

An embodiment of the present disclosure is a tampon. The tampon includes an outer carrier component including an inner surface that defines an internal void. The tampon also includes an absorbent component that is elongate along an axis and is disposed in the internal void. The absorbent component includes an outer surface that extends about the axis and faces the inner surface. The absorbent component further includes a composite fibrous web of staple cellulosic fibers and a meltspun web of filaments entangled with the web of staple cellulosic fibers. The composite fibrous web can be in a compressed configuration in the internal void such that at least portion of the outer surface of the absorbent component is defined by the meltspun web of filaments. The tampon can include a withdrawal cord coupled to the absorbent component and extending relative to the absorbent component in a direction away from the absorbent component.

An embodiment of the present disclosure is a composite fibrous web configured to be compressed so as to transition into an absorbent component of a tampon. The composite fibrous web includes a meltspun web of filaments having a first side and a second side opposed to the first side along a thickness direction. The web of staple cellulosic fibers can be adjacent to one of the first and second sides of the meltspun web of filaments along the thickness direction and further extends along a length direction that is perpendicular to the thickness direction. The web of staple cellulosic fibers can be entangled with the filaments of the meltspun web so as to define the composite fibrous web. The composite fibrous web is configured to transition from a first uncompressed configuration into a second compressed configuration.

Another embodiment of the present disclosure is a method forming a tampon. The method includes the step of advancing a fibrous assembly along a machine direction toward a consolidation unit. The fibrous assembly including a fibrous web of staple cellulosic fibers and a meltspun web of filaments adjacent to the fibrous web of staple cellulosic fibers along a vertical direction that is perpendicular to the machine direction. The method includes the step of consolidating the fibrous assembly in the consolidation unit; such that, the fibrous web of staple cellulosic fibers are substantially entangled with the filaments of the meltspun web so as to define a composite fibrous web.

BRIEF DESCRIPTION OF THE DRAWINGS

The foregoing summary, as well as the following detailed description of illustrative embodiments of the present application, will be better understood when read in conjunction with the appended drawings. For purposes of illustrating the present application, the drawings show exemplary embodiments of the present disclosure. It should be understood, however, that the present disclosure is not limited to the precise arrangements and instrumentalities shown in the drawings. In the drawings.

DETAILED DESCRIPTION OF ILLUSTRATIVE EMBODIMENTS

Figure 1:
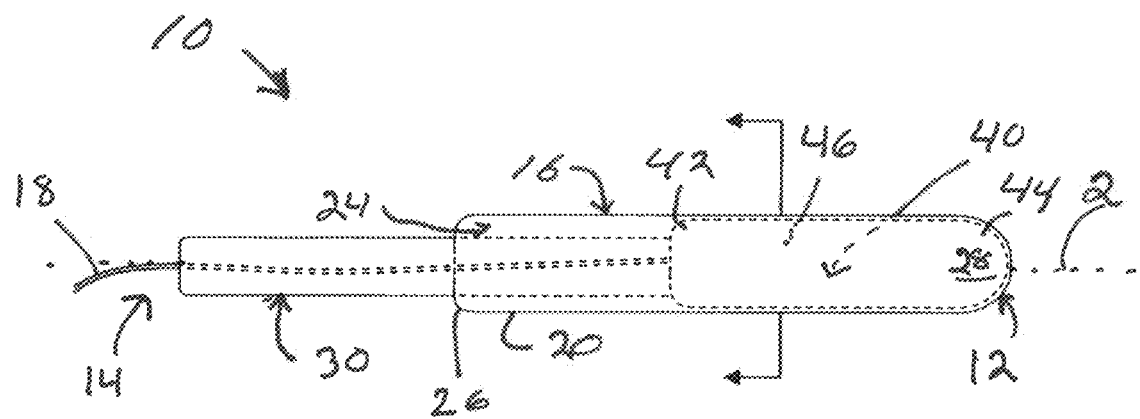
FIG. 1 is a schematic side view of a tampon according to an embodiment of the present disclosure.

Referring to FIG. 1, embodiments of the present disclosure include an absorbent article, such as a tampon 10. The tampon 10 is elongate along an axis 2 and includes an insertion end 12 and a withdrawal end 14 spaced from the insertion end 12 along the axis 2. The tampon 10 includes an outer carrier component 16, illustrated as a tubular body, an absorbent component 40 disposed within the outer carrier component 16, and a withdraw cord 18 coupled to the absorbent component 40 and extending relative to the absorbent component 40 out the withdrawal end 14 of the tampon 10. The tampon 10 as illustrated includes an applicator 30 disposed in the internal void 24 and adjacent to the absorbent component 40. In some instances, the tampon 10 does not include the applicator 30. Tampons without applicators are referred to as digital tampons and tampons with applicators are called applicator tampons. The applicator 30 is an optional component and is not essential.

Figure 2:
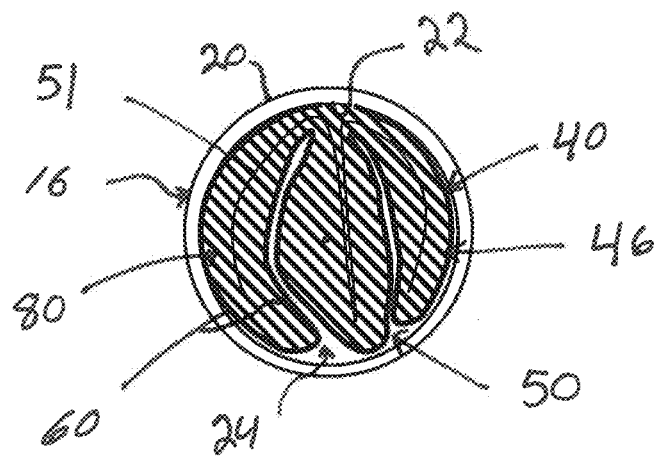
FIG. 2 is a cross-sectional view of the tampon taken along line 2-2 in FIG. 1.

Referring to FIGS. 1 and 2, the outer carrier component 16 includes an elongated tubular body 20 that defines an inner surface 22. The inner surface 22, in turn, defines an internal void 24. The outer carrier component 16 includes opposed first and second end 26 and 28, respectively. The second end 28 can be a forward end, which can also define the tampon insertion end 12. The forward end 28 can be partially or substantially open such that absorbent component 40 can pushed out of the outer carrier component 16 during use. The outer carrier component 16 can be formed of paperboard or a polymeric material that is suitable for use as a hygiene article. The outer carrier component 16, and the tubular body 20, in particular, can help maintain the absorbent component in a compressed state as further explained below.

Continuing with FIGS. 1 and 2, the absorbent component 40 is disposed in the internal void 24 of the outer carrier component 16 in a compressed configuration. The absorbent component 40 can be elongate along the axis 2 and include a first end 42, a second end 44 opposed to the first end and 44, and an outer surface 46 that extends about the axis 2 and that faces the inner surface 22 of the outer carrier component 16. The absorbent component 40 can have a generally cylindrical shape when in the compressed configuration. The shape of the outer carrier component 16 can at least partially define the shape of the absorbent component 40. However, the shape of the outer carrier component 16 and the absorbent component 40 is not limited to a cylindrical shape or a circular cross-section shape. Other non-cylindrical shapes or non-circular cross-sectional shapes can be used, as needed.

Turning to FIG. 2, the absorbent component 40 includes a composite fibrous web 50 in a compressed configuration inside the outer carrier component 16. The composite fibrous web 50 includes a web of staple cellulosic fibers 80 and a meltspun web of filaments 60 that are entangled with the web of staple cellulosic fibers 80. The meltspun web of filaments 60 may be referred to as a "meltspun web 60". The web staple cellulosic fibers 80 may be referred to a "cellulosic staple fiber web 80". The composite fibrous web 50 is shown in FIG. 2 in a folded, compressed configuration, such that the composite fibrous web 50 overlaps about itself. In particular, because the composite fibrous web 50 is a two-layered structure, as further detailed below, portions of the meltspun web 60 are adjacent to each other and portions of the web of staple cellulosic fibers 80 are adjacent to each other when the composite fibrous web 50 is the folded configuration. For instance, an interface line 51 illustrates where adjacent portions of the cellulosic staple fiber web 80 abut when in the folded configuration. The composite fibrous web 50 is not limited to being compressed into a folded configuration as show in FIG. 2. In alternative embodiments, the composite fibrous web 50 can have a spiral wound configuration whereby the composite fibrous web is wound about the axis 2 (not shown). In still other embodiments, the composite fibrous can be compressed along a direction offset with respect to a length of the absorbent component 40.

Continuing with FIG. 2, when the composite fibrous web 50 is compressed, the meltspun web 60 can define a substantial portion of the outer surface 46 of the absorbent component 40. In accordance with the illustrated embodiment, when the composite fibrous web 50 is in the folded configuration, portions of the meltspun web 60 are disposed outwardly to define a substantial portion of the outer surface 46 of the absorbent component 40. In this regard, the meltspun web 60 can define a full or partial covering or overwrap for the cellulosic staple fiber web 80. However, the meltspun web 60 is substantially entangled with the cellulosic staple fiber web 80, thereby creating a covering that is monolithic with the absorbent component 40.

Prior to composite fibrous web 50 transitioning into the compressed configuration, the composite fibrous web 50 has uncompressed and planar configuration, similar to textile roll goods that can be wound, slit into desired shapes for assembly into the tampon.

Figure 3:
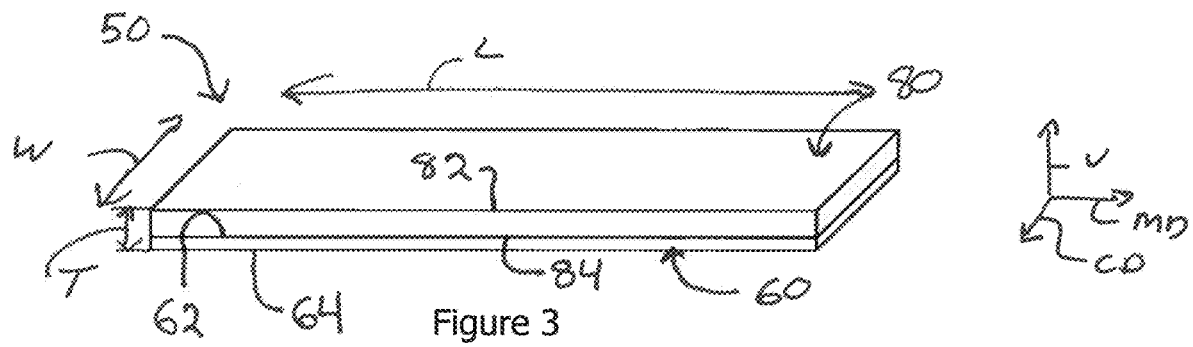
FIG. 3 is a schematic perspective view of a composite fibrous web used to form the absorbent component in FIG. 2.
Figure 4:
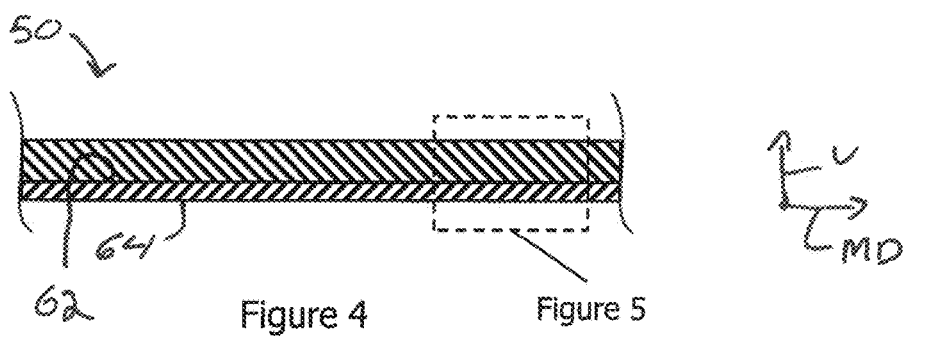
FIG. 4 is a schematic side sectional of view of the composite fibrous web shown in FIG. 3.
Figure 5:
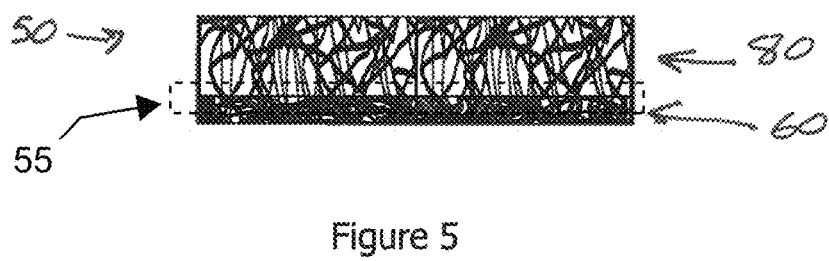
FIG. 5 is a detailed sectional view of the composite fibrous web shown in FIG. 4.

Turning now to FIGS. 3-5, a composite fibrous web 50 is illustrated in an uncompressed configuration. The composite fibrous web 50 includes a first layer of meltspun web of filaments 60 and a second layer of the web of staple cellulosic fibers 80. In accordance with the illustrated embodiment, the meltspun web of filaments 60 has a first side 62 (also a web face 62) and a second side 64 (or web back 64) opposed to the first side 62 along a vertical direction V. The web of staple cellulosic fibers 80 has a first side 82 (also a web face 82) and a second side 84 (or web back 84) opposed to the first side 82 along the vertical direction V. The web of staple cellulosic fibers 80 is disposed adjacent to the second side 64 of the meltspun web of filaments 60 along the vertical direction V. The web of staple cellulosic fibers 80 can be disposed along the first side 62 as well.

Continuing with FIGS. 3-5, the meltspun web 60 is substantially entangled with the cellulosic staple fiber web 80 so as to define monolithic, composite fibrous web 50. More specifically, it is believed that portions of the web of staple cellulosic fibers are entangled with each other and with the filaments of the meltspun web 60. In accordance with illustrated embodiment, the composite fibrous web 50 is a hydro-entangled composite fibrous web.

Continuing with FIGS. 3-5, the meltspun web 60 is entangled with web of staple cellulosic fibers at an entanglement zone 55. In this entanglement zone 55, a plurality of filaments of the meltspun web 50 are entangled and knotted with a plurality of the staple fiber of the web of staple cellulosic fibers 80 using the techniques described herein. Advantageously, the entanglement zone 55 is devoid of an adhesive, stitching, or combination thereof. In doing so, composite fibrous web 50 is constructed such that the meltspun web 60 is substantially integrated with the cellulosic web of fibers 80. The web of filaments are entangled with the staple cellulosic fibers such that if a one attempted to delaminate the meltspun web 60 from the web of cellulosic fibers 80, the structural integrity of the each individual web 60 and 80 would be destroyed. In other words, the strength of entanglement at the zone 55 is greater than the bond strength among individual fibers of each meltspun web 60 and web of cellulosic fibers 80. Accordingly, the web of meltspun filaments 60 and the web of cellulosic fibers 80 are not merely laying adjacent to each other. Rather, the web of meltspun filaments 60 and the web of cellulosic fibers 80 define a monolithic composite web 50 that includes filaments on one side, and staple fibers on the other side.

Figure 6:
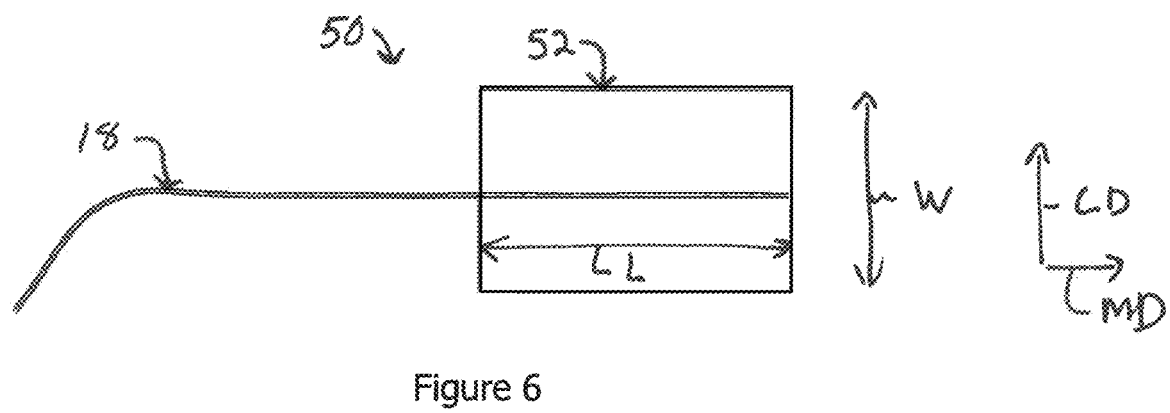
FIG. 6 is a plan view of a pledget for the tampon illustrated in FIG. 1 and cut from the composite fibrous web shown in FIGS. 3-5.

Continuing with FIGS. 3-5, the meltspun web 60 and web of staple cellulosic fibers 80 are substantially coplanar with respect each other. Specifically, the composite fibrous web 50 can be an elongate material having a length L (see FIG. 6) that extends along a machine direction MD, a width W along a cross direction CD that is perpendicular to the machine direction MD, and a thickness T that is perpendicular to the length L and the width W. As illustrated in FIG. 3, the meltspun web 60 and web of staple cellulosic fibers 80 can be coplanar with respect each other along an entirety of the length L and the width W of composite fibrous web 50. Accordingly, as shown in FIG. 6, the composite fibrous web 50 can be cut or formed into a pledget 52 (or pad) that includes the meltspun web 60 and web of cellulosic fibers 80. The withdrawal cord 18 can be coupled to pledget 52 as is known in the art. The pledget 52, or pad, is compressed into the generally cylindrical shape of the absorbent component 40 as described above as shown in FIGS. 1 and 2.

The composite fibrous web 50 has a relatively low weight proportion of non-absorbent components relative to absorbent components. For instance, the composite fibrous web 50 has a basis weight in the range of about 100 grams per square meter to about 330 grams per square meter. In one embodiment, the basis weight of the composite fibrous web 50 is in the range of about 150 grams per square meter to about 250 grams per square meter. In another embodiment, the basis weight is in the range of about 170 grams per square meter to about 200 grams per square meter. The meltspun web 60 has a basis weight in the range of about 8 or about 10 grams per square meter to about 30 grams per square meter. Although in some cases, the meltspun web 60 can have a basis weight could be as a low as about 2.5 or 5.0 grams per square meter. In one embodiment, the meltspun web 60 has a basis weight in the range of about 10 grams per square meter to about 18 grams per square meter. The cellulosic staple fiber web 80, which defines the absorbent component in the composite fibrous web 50, can have a basis weight in the range of about 85 grams per square meter to about 280 grams per square meter. Across the range of basis weights discussed above, in at least one example, the meltspun web 60 comprises about 2.5% to about 15.0% by weight of the composite fibrous web 50. The low proportion of the meltspun web 60 (the substantially non-absorbent material) relative to the cellulosic staple fiber web 80 (the absorbent material) facilitates the desired absorption characteristics of the absorbent component 40 in use. The percentage by weight as used herein is determined using the basis weight of the composite fibrous web 50 off of the processing line. The basis weight of the meltspun web 60 is its basis weight prior to consolidation with the cellulosic staple fiber web 80, as further detailed below. The basis weight referred to herein can be determined according to ISO 9073-1:1989, Textiles—Test methods for nonwovens—Part 1: Determination of mass per unit area."

The meltspun web 60 can be any melt-processed nonwoven materials with spun filaments. For instance, the melt spun web 60 can be A) at least one spunbond nonwoven, B) at least one meltblown nonwoven, or C) a composite of the spunbond and meltblown nonwovens. One or a plurality of the meltspun materials can define the meltspun web 60. For example, a spunbond nonwoven may include one or a plurality of spunbond layers defining the meltspun web 60. In one embodiment, the meltspun web of filaments is a spunbond nonwoven.

The meltspun web of filaments 60 can be formed using a range of thermoplastic polymers. For example, the meltspun web can include polypropylene (PP) filaments, polyethylene terephthalate (PET) filaments, polyamide (PA) filaments, polyethylene (PE) filaments, or polylactic acid (PLA) filaments. The meltspun web 60 can include homogenous filaments, bicomponent filaments, or multi-component filaments. Furthermore, the cross-sectional shape of the filaments can be varied and include a circular, trilobal, multi-lobed shapes and other. The denier of filaments can range from about 0.5 to about 8 denier.

The meltspun web 60 can be a thermally bonded web. Specifically, the meltspun web 60 can be a flat bonded web, a point bonded web, or a through-air bonded web. In one embodiment, the meltspun web 60 is a point bonded web. Point bonded webs define generally lower bonding surface areas and can be yield greater filament movement in response to applied forces, while still maintaining adequate dimensional stability. The point bond web can be referred to as a lightly bonded web. It is believed that light bonding facilitates entanglement with the web of cellulosic fibers due to increased fiber mobility that point bonding provides. As discussed above, the meltspun web 60 can have a basis weight in the range of about 2.5 or about 5.0 grams per square meter to about 30 grams per square meter.

The web of cellulosic fibers 80 can be a dry laid fibrous assembly of staple fibers. Details concerning how the web of staple cellulosic fibers is formed are further discussed below. As used herein, the web of staple cellulosic fibers includes synthetic of manmade cellulosic fiber and natural cellulosic fibers. Manmade cellulosic fibers include, but are not limited to: regenerated cellulose; viscose; rayon; lyocell; cellulose nitrate; carboxymethyl cellulose, and the like. Natural cellulosic fibers include, but are not limited to: cotton; wood pulp; jute; hemp; sphagnum, and the like. In one embodiment, the web of staple cellulosic fibers are viscose fibers. For viscose fibers, the staple length can be about 5 mm to about 50 mm. The denier can be about 2 to about 6 and the staple fiber size of from about 15 microns to about 28 microns. In another embodiment, the web of staple cellulosic fibers are cotton fibers. When cotton fibers are used, the cotton fibers have a staple length of about 5 millimeters (mm) to about 30 mm. The cotton fibers can generally have a fiber size of about 150 microns to about 280 microns. The cotton fibers can also be bleached if desired. In a further embodiment, the web of staple cellulosic fibers includes a blend of viscose and cotton fibers. Suitable blends include a blend of about 15% cotton to about 85% viscose; about 70% cotton to about 30% viscose; about 60% cotton to about 40% viscose; about 25% cotton to about 75% viscose; and about 6% cotton to about 94% viscose. Other blends are possible.

In accordance with one embodiment of the present disclosure, the composite fibrous web 50 is a hydro-entangled web that includes a thermally bonded meltspun web of filaments 60 and a web of staple cellulosic fibers entangled with the meltspun web of filaments 60. Such a hydro-entangled web has a basis weight in the range of about 100 grams per square meter to about 300 grams per square meter. In some embodiments, the basis weight is about 170 grams per square meter to about 200 grams per square meter. Furthermore, the meltspun web of filaments comprises about 2.50% to about 15.0% by weight of the hydro-entangled web. In some embodiments, the meltspun web of filaments comprises about 5.0% to about 12.0% by weight of the hydro-entangled web. In one embodiment of such a hydro-entangled web, the cellulosic fibers are viscose fibers. In another embodiment of such a hydro-entangled web, the cellulosic fibers are cotton fibers. In yet a further embodiment of such a hydro-entangled web, the cellulosic fibers include a blend of viscose and cotton fibers.

Figure 7:
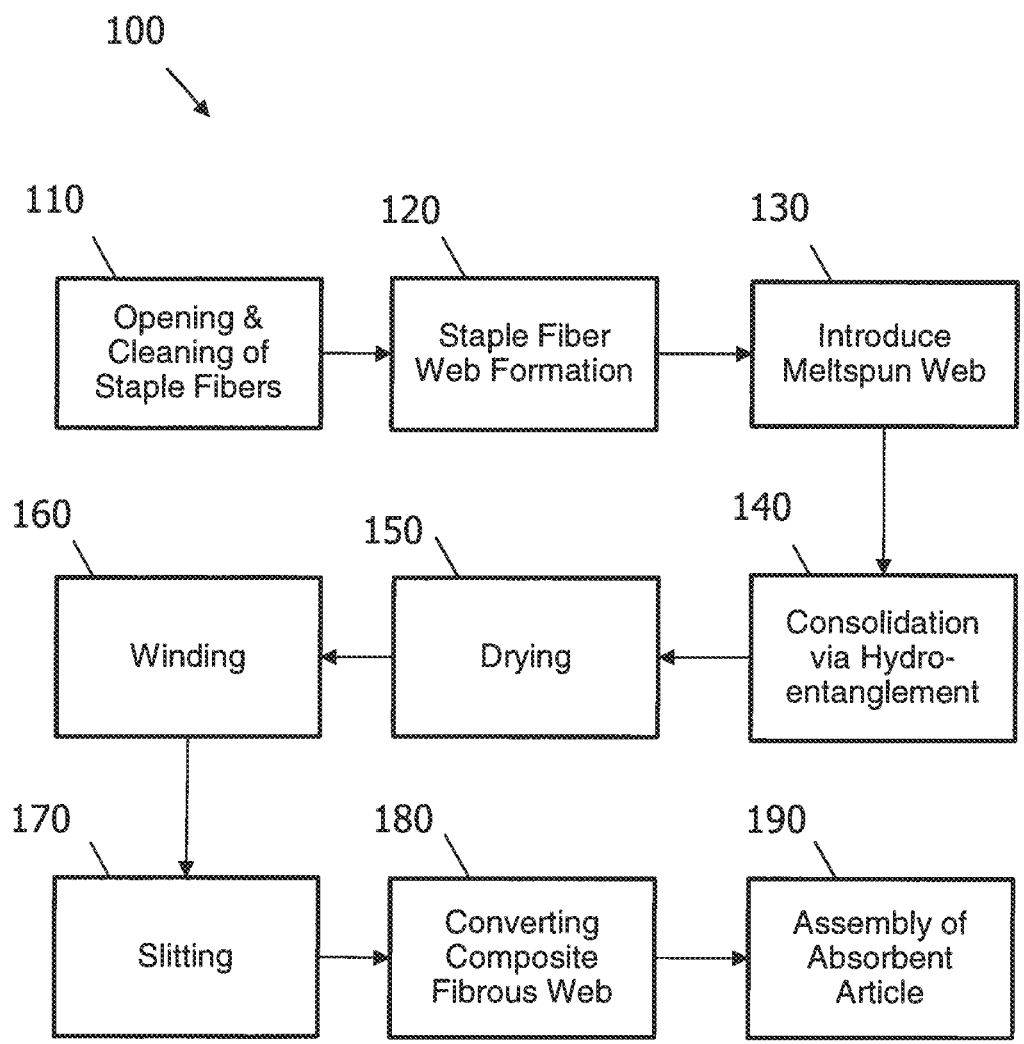
FIG. 7 is a process flow diagram for a method of making the tampon illustrated in FIG. 1.
Figure 8:
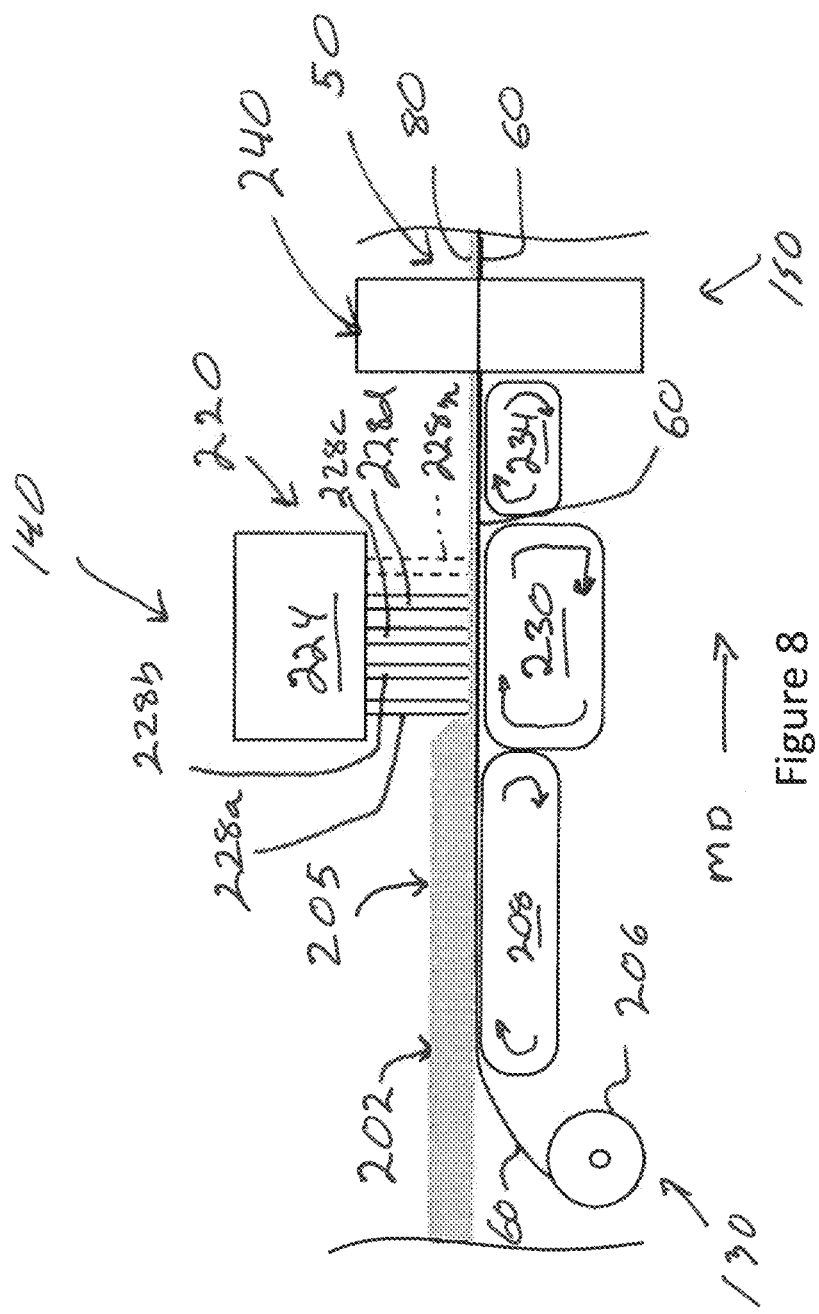
FIG. 8 is a schematic of a portion of a manufacturing line used to form the tampon illustrated in FIG. 1.

Turning now to FIGS. 7 and 8, a process 100 for manufacturing the tampon 10 is illustrated. Specifically, the process 100 as illustrated is designed to form a composite fibrous web 50 as described above, which is then used to construct the tampon 10 illustrated in FIG. 1. The process 100 includes a fiber preparation step 110. In step 110, bales of cellulosic fibers are opened and larger fiber tufts taken from the bale are reduced in size. The fiber preparation step may include a blending step where the tufts are further opened and a predetermined weight of fibers are deposited onto a conveyer. Optional coarse and fine opening phases further individualize the staple fiber. From there, a feeding device introduces a loose, random assembly of staple fibers to web formation equipment, such as one or more cards.

In step 120, web formation transforms the random assembly of loose fibers into an ordered fibrous web via cards or airlaid machines, depending on fiber type and design considerations. One or more cross-lappers may be used to adjust the weight and/or fiber orientation. Furthermore, longitudinal lappers may be used. Step 120 results in a fibrous web of staple fibers 202 (FIG. 8) that is advanced along the machine direction MD toward the next process step.

Referring to FIGS. 7 and 8, after the web formation step 130, the meltspun web 60 is introduced to the underside of the fibrous web of staple fibers 202 in step 140. FIG. 8 illustrates a portion of the manufacturing line for making a tampon. During step 130, the meltspun web 60 may be unwound from roll stock 206. A first conveyer 208 advances the meltspun web 60 and fibrous web of staple fibers 202 in the machine direction MD toward the consolidation unit 220. The meltspun web 60 and fibrous web of staple fibers 202 prior to consolidation can be referred to as a pre-entangled composite 205.

In step 140, the pre-entangled composite 205 is consolidated by unit 220. In particular, during step 140, the fibrous web of staple fibers 202 are substantially entangled with the filaments of the meltspun web 60 so as to define the composite fibrous web 50. In accordance with illustrated embodiment in FIGS. 7 and 8, the consolidation unit 220 can be hydro-entanglement unit. The hydro-entanglement unit 220 includes a high pressure module 224 that includes a series water jet nozzle assemblies 228a, 228b, 228c, 228d . . . 228n that are spaced apart along the machine direction MD. The number of water nozzle jet assemblies can be about 2 to about 10. Four water jet nozzle assemblies are shown for illustrative purposes. More than four or less than four could be used. Each water jet nozzle assembly 228a-228d is configured to eject a plurality of high pressure water jets into the pre-entangled composite fibrous web 205. A forming surface or screen 230 carries the pre-entangled composite fibrous web 205 along each water jet nozzle assembly 228a-228d where high pressure jets of water cause the staple fibers to entangle with each other and with the filaments of the meltspun web 60. In accordance with an embodiment of the present disclosure, the hydro-entangling step 140 includes subjecting the pre-entangled composite fibrous web 205 water jets at a pressure of about 100 bar to about 300 bar. A second conveyer 234 advances the composite fibrous web 50 toward the next process step.

Referring to FIGS. 7 and 8, in step 150 the composite fibrous web 50 is introduced to a drying unit 240 to remove moisture from the composite fibrous web 50. Following the drying step 150, the composite fibrous web 50 may have a basis weight in the range of about 100 grams per square meter to about 330 grams per square meter. In one embodiment, the basis weight of the composite fibrous web 50 is in the range of about 150 grams per square meter to about 250 grams per square meter. In another embodiment, the basis weight is in the range of about 170 grams per square meter to about 200 grams per square meter. The meltspun web 60 has a basis weight in the range of about 2.5 grams per square meter to about 30 grams per square meter. The cellulosic staple fiber web 80, which defines the absorbent component in the composite fibrous web 50, can have a basis weight in the range of about 85 grams per square meter to about 280 grams per square meter. The composite fibrous web 50 is configured so that the meltspun web 60 comprises about 2.5% to about 15.0% by weight of the composite fibrous web 50.

Turning to FIG. 7, after the drying step 150, step 160 includes winding the composite fibrous web 50 into roll-good form. After the winding step 160, step 170 includes slitting the composite fibrous web into strips of sliver or even wide goods. In step 180, the slit composite fibrous webs 50 are converted into components for tampon assembly. For example, the slits of the composite fibrous web 50 may be cut in to pledget 52, as described above. In step 180, the withdrawal cord 18 may be coupled to the pledget 52. Following step 180, the tampon 10 is assembled in step 190. Specifically, the pledget 52 is compressed into a cylindrically shaped body to define the absorbent component 40. The absorbent component 40 is then disposed in the outer carrier component 16 as illustrated in FIG. 1. Next, optional applicators are disposed in the outer carrier component 16. The assembled tampon 10 is then packaged and prepared for shipment to the distributor.

As opposed to the current methods of manufacturing tampons, which require multiple, separate pieces of machinery, the methods described herein are efficient and require only one piece of machinery to produce the tampon product, i.e., they are continuous. In doing so, there are considerably fewer chances for the outer covering to become detached from the absorbent component, thereby reducing contamination and chances that the absorbent component may come into contact with a sensitive vaginal cavity. Further, another advantage of the present disclosure is that the methods described herein preclude the need for costly bale openers, fiber cleaning machines, carding machines, among others, at the point of tampon manufacture, thereby reducing material cost and capital requirements for tampon manufacturers.

It will be appreciated by those skilled in the art that various modifications and alterations of the present disclosure can be made without departing from the broad scope of the appended claims. Some of these have been discussed above and others will be apparent to those skilled in the art. The scope of the present disclosure is limited only by the claims.

We claim:

1. A tampon article, comprising:
an outer carrier component including an inner surface that defines an internal void;
an absorbent component that is elongate along an axis and is disposed in the internal void, the absorbent component including an outer surface that extends about the axis and faces the inner surface, the absorbent component further including a compressed composite fibrous web that includes a) a web of staple cellulosic fibers, and b) a meltspun web of filaments having a first side, a second side opposed to the first side along a thickness, a length perpendicular to the thickness, and a width perpendicular to the length and the thickness, where the width is greater than the thickness and smaller than the length, wherein the meltspun web of filaments is entangled with the web of staple cellulosic fibers so that the web of staple cellulosic fibers is 1) coplanar with respect to the meltspun web of filaments and 2) extends along an entirety of the length and the entirety of the width of the meltspun web of filaments, wherein the compressed composite fibrous web is compressed in the internal void such that at least a portion of the outer surface of the absorbent component is defined by the meltspun web of filaments.

2. The tampon article of claim 1, wherein the web of staple cellulosic fibers is one of a) web of viscose fibers, b) a web of cotton fibers, orb) a web of a blended viscose fibers and cotton fibers.

3. The tampon article of claim 1, wherein the meltspun web comprises about 2.50% to about 15.0% by weight of the absorbent component.

4. The tampon article of claim 1, wherein the meltspun web is at least one of: A) at least one spunbond nonwoven, or B) at least one meltblown nonwoven.

5. The tampon article of claim 1, wherein the filaments of the meltspun web are polypropylene filaments, polyethylene terephthalate filaments, polyamide filaments, polyethylene filaments, or poly lactic acid filaments.

6. The tampon article of claim 1, wherein the composite fibrous web is a hydro-entangled web of the meltspun web of filaments entangled with the web of staple cellulosic fibers and the meltspun web comprises about 2.50% to about 15.0% by weight of the composite fibrous web.

7. The tampon article of claim 1, wherein the composite fibrous web is folded into the compressed configuration.

8. The tampon article of claim 1, wherein the composite fibrous web is spiral wound into the compressed configuration.

9. The tampon article of claim 1, wherein the composite fibrous web is substantially cylindrical.

10. The tampon article of claim 1, wherein the absorbent component includes an entanglement zone, wherein the entanglement zone is where a plurality of filaments of the meltspun web of filaments are entangled with a plurality of staple fibers of the web of cellulosic staple fibers.

11. The tampon article of claim 10, wherein the plurality of filaments are entangled and knotted with the plurality of the cellulosic fibers.

12. The tampon article of claim 10, wherein the entanglement zone is devoid of an adhesive, stitching, or combination thereof.

13. The tampon article of claim 1, further comprising a withdrawal cord coupled to the absorbent component and extending relative to the absorbent component in a direction away from the absorbent component.

14. The tampon article of claim 1, wherein the composite fibrous web is monolithic.

15. A composite fibrous web configured to be compressed so as to transition into an absorbent component of a tampon article, the composite fibrous web comprising:
    a meltspun web of filaments having a first side, a second side opposed to the first side along a thickness, a length perpendicular to the thickness, and a width perpendicular to the length and the thickness, where the width is greater than the thickness and smaller than the length;
    a web of staple cellulosic fibers adjacent to one of the first and second sides of the meltspun web of filaments, such that, the web of staple cellulosic fibers is 1) coplanar with respect to the meltspun web of filaments and 2) extends along an entirety of the length and the entirety of the width of the meltspun web of filaments; and
    an entanglement zone where the web of staple cellulosic fibers are entangled with the filaments of the meltspun web of filaments so as to define the composite fibrous web, wherein the composite fibrous web is configured to transition from a first uncompressed configuration into a second compressed configuration.

16. The composite fibrous web of claim 15, further comprising a hydro-entangled composite fibrous web that includes the meltspun web of filaments and the web of staple cellulosic fibers.

17. The composite fibrous web of claim 15, wherein the meltspun web of filaments comprises about 2.50% to about 15.0% by weight of the composite fibrous web.

18. The composite fibrous web of claim 15, wherein the composite fibrous web has a basis weight in the range of about 100 grams per square meter to about 300 grams per square meter.

19. The composite fibrous web of claim 15, wherein the web of staple cellulosic fibers are viscose fibers, cotton fibers, or a blend of viscose and cotton fibers.

20. The composite fibrous web of claim 19, wherein the meltspun web of filaments includes at least one of: A) at least one spunbond nonwoven, and B) at least one meltblown nonwoven.

21. The composite fibrous web of claim 20, wherein the meltspun web of filaments is a thermally bonded meltspun web.

22. The composite fibrous web of claim 21, wherein the thermally bonded meltspun web is a point bonded web.

23. The composite fibrous web of claim 15, wherein the filaments of the meltspun web are polypropylene filaments, polyethylene terephthalate filaments, polyamide filaments, polyethylene filaments, or polylactic acid filaments.

24. The composite fibrous web of claim 15, wherein the filaments of the meltspun web include homogenous filaments, bicomponent filaments, and multi-component filaments.

25. The composite fibrous web of claim 15, further comprising a hydro-entangled web that includes the meltspun web of filaments and the web of staple cellulosic fibers, wherein the meltspun web of filaments is a thermally bonded web, and wherein A) the hydro-entangled web has a basis weight in the range of about 100 grams per square meter to about 300 grams per square meter, and B) the meltspun web of filaments comprises about 2.50% to about 15.0% by weight of the hydro-entangled web.

26. The composite fibrous web of claim 15, wherein the composite fibrous web is monolithic.

* * * * *